United States Patent [19]

Brown et al.

[11] Patent Number: 4,780,559

[45] Date of Patent: Oct. 25, 1988

[54] PROCESS FOR PREPARING ORGANIC FLUORIDES

[75] Inventors: Stephen J. Brown, Ontario, Canada; James H. Clark, York, England

[73] Assignee: Imperial Chemical Industries PLC, London, England

[21] Appl. No.: 816,432

[22] Filed: Jan. 1, 1986

[30] Foreign Application Priority Data

Jan. 4, 1985 [GB] United Kingdom ............... 8500180

[51] Int. Cl.$^4$ ........................................ C07C 121/60
[52] U.S. Cl. .................................. 558/425; 568/933; 568/938; 568/939; 570/134; 570/145
[58] Field of Search ............... 558/425; 570/134, 145, 570/141; 568/938, 931, 933, 939

[56] References Cited

U.S. PATENT DOCUMENTS 3,899,542  8/1975  Starks et al. .................... 260/658 R
4,590,315  5/1986  Maul et al. ......................... 558/425

OTHER PUBLICATIONS

Brown et al, "J. Chem. Soc. (London) Chem. Commun.", (1983), 21, 1256–7.

*Primary Examiner*—Anton H. Sutto
*Attorney, Agent, or Firm*—Cushman, Darby & Cushman

[57] ABSTRACT

A method for the preparation of organic fluorides which comprises reacting a quaternary phosphonium fluoride or bifluoride with an organic substrate having at least one atom or group capable of being replaced by a fluorine atom.

4 Claims, No Drawings

PROCESS FOR PREPARING ORGANIC FLUORIDES

This invention relates to a chemical process and more particularly to a method for the preparation of organic fluorides.

It is known (J. Amer. Chem. Soc., 96, 2250, 1974) to make organic fluorides by reacting organic substrates containing suitable leaving groups, for example chlorine and bromine atoms, with the 18-Crown-6 complex of potassium fluoride in aprotic organic solvents.

It has now been found that the same substitution reaction may be effected more readily by employing a quaternary phosphonium fluoride or bifluoride, as fluorinating agent.

Accordingly, the invention provides a method for the preparation of organic fluorides which comprises reacting a quaternary phosphonium fluoride or bifluoride with an organic substrate having at least one atom or group capable of being replaced by a fluorine atom.

Suitable organic substrates include compounds of the formula:

$$Q-X$$

wherein Q represents an alkyl, aralkyl, aryl or heterocyclic radical and X represents a replaceable atom or group.

Alkyl radicals which may be represented by Q include methyl, ethyl, heptyl, decyl, octadecyl and higher alkyl radicals. Aralkyl radicals include benzyl whilst aryl radicals particularly include those having at least one electronegative substituent, for example chlorine, nitro, cyano and trifluoromethyl.

Leaving groups which may be represented by X include chlorine, bromine and iodine atoms and nitro and sulpho groups.

The radical Q may carry substituents including other replaceable atoms or groups such that the substrate has the formula:

$$Q^1X_n$$

wherein $Q^1$ represents an aliphatic, arylaliphatic, aromatic or heterocyclic residue, X represents a replaceable atom or group and n is an integer of at least 2. In this case the replaceable atoms or groups may be the same or different and the reaction conditions may be adjusted as desired to replace one or more of these atoms or groups by fluorine atoms.

Examples of suitable organic substrates include 1-iodoheptane, dibromomethane, 1,2-dichloroethane, benzyl chloride, benzyl bromide, 4-chlorobenzotrifluoride, 3,4-dichlorobenzotrifluoride, 3,4,5-trichlorobenzotrifluoride, 2-chloro-6-nitrobenzonitrile, 1-chloro-2,4-dinitrobenzene and 3,4-dichloronitrobenzene.

Quaternary phosphonium fluorides and bifluorides which may be used in accordance with the invention include compounds of the formula:

$$R_3R^1P^+X^-$$

wherein R represents an optionally substituted aryl radical, $R^1$ represents an optionally substituted alkyl or optionally substituted aryl radical and $X^-$ represents an anion of the formula:

$$F(HF)_x^-$$

wherein x is an integer from 0 to 4, especially 1.

The quaternary phosphonium compounds can be conveniently prepared by passage of the corresponding chloride, bromide or iodide through an ion-exchange resin previously charged with hydrofluoric acid or a solution of another fluoride such as ammonium bifluoride or potassium fluoride. For example, $Ph_4P^+Br^-$ can be quantitatively converted to $Ph_4P^+HF_2^-$ by passage of a solution of the commercial bromide through a commercial ion-exchange resin such as Amberlite IRA 410 which has been previously treated with aqueous sodium hydroxide followed by hydrofluoric acid. The resulting solution of the bifluoride is best concentrated by evaporation and then treated with a solvent such as ether to precipitate out the product.

Alternatively, reagents can be prepared starting from a phosphine and an aryl bromide or iodide. For example, triphenyl phosphine is reacted with 4-iodoanisole in xylene in the presence of palladium acetate according to the method of Migita, et al. in Bull. Chem. Soc. Jap. 56, 2869 (1983), to give 4-methoxyphenyltriphenylphosphonium iodide which can then be converted to the desired reagent as described above. In this way it is possible to prepare a variety of quaternary phosphonium compounds containing substituted aryl radicals.

Reaction between the organic substrate and the phosphonium compound is conveniently performed at temperatures up to 250° C. The reagent is usually employed in at least an equivalent amount relative to the leaving group although in some cases a twofold excess of reagent is preferred so as to allow for the possibility of formation of polyfluorides which may not be reactive at lower temperatures. Reactions may be carried out in the absence of solvent taking advantage of the good solubility of the reagents in many organic liquids. Alternatively, solvents may be employed including both polar and non-polar aprotic solvents.

When the reaction is substantially complete, the organic fluoride may be isolated in a conventional manner, for example by distillation from the bulk mixture or by addition of ether to remove the organic materials followed by product purification. The spent reagent mixture can be conveniently regenerated by passage through an ion exchange resin charged with hydrofluoric acid as described above. No significant loss in reagent activity is observed after several regenerations carried out in this way. Similarly, the resin itself can be regenerated after use by treatment with hydrofluoric acid.

The reagents described offer several advantages over alternative reagents for the preparation of organic fluorides. These include high thermal stability, high solubility, low hygroscopicity, high activity, as well as ease of preparation. For example, $Ph_4P^+HF_2^-$ is a stable white solid, which can be dried by conventional methods and does not decompose at temperatures below 230° C. This can be contrasted with the quaternary ammonium fluorides which cannot be easily dried and undergo thermal decomposition at temperatures below 100° C. The solubility of $Ph_4P^+HF_2^-$ is good in many solvents including those of low polarity such as halocarbons and aromatics. This can be contrasted with the alkali metal fluorides which show good solubility in only a few protonic solvents such as water, hydrofluoric acid and carboxylic acids. Furthermore, reagents such as the bifluorides show high activity as fluorinating agents unlike the largely unreactive bifluorides of the alkali metals and quaternary ammoniums. Thus, reagent preparation can be carried out under conditions in which there is excess hydrofluoric acid present (as described earlier) with no need to subsequently reduce the resulting bifluoride to the fluoride.

Reagent activity is high when compared to many other fluoride reagents. For example, benzyl bromide reacts with two mole equivalents of $Ph_4P^+HF_2^-$ at 52° C. in acetonitrile to give quantitative conversion to benzyl fluoride within two hours. This can be compared with the same reaction carried out with a mixture of potassium fluoride and 18-crown-6 (in excess) which gives only 50% conversion to benzyl fluoride after eleven and a half hours at 82° C. (Liotta and Harris, J. Amer. Chem. Soc., 96, 2250 (1974). On this basis, the reactivity of $Ph_4P^{+4}HF_2^-$ is estimated to be about one hundred times as great as that of KF-18-crown-6.

The quaternary phosphonium fluorides and bifluorides may also be used to effect oligomerisation of olefins such as hexafluoropropene.

The invention is illustrated but not limited by the following Examples.

EXAMPLE 1

Dried $Ph_4P^+HF_2^-$ (1.50 g) was dissolved in acetonitrile (25 cm$^3$). Benzyl bromide was then added (0.5 cm) to the phosphonium salt solution and the mixture was heated at 52° C. for two hours at which stage complete conversion to benzyl fluoride had been achieved. The bulk of the solvent was then removed under reduced pressure and diethyl ether sufficient to precipitate the phosphonium salt was added, the salt then being removed by filtration.

The diethyl ether and acetonitrile were then removed by rotary evaporation to give analytically pure benzyl fluoride.

EXAMPLE 2

The same reaction as described in Example 1 but using triphenylisopropylphosphonium bifluoride rather than tetraphenylphosphonium fluoride gave 62% conversion to benzyl fluoride after two hours reaction in acetonitrile at 52° C.

EXAMPLE 3

Dried tetraphenylphosphonium bifluoride (2.68 g, 7.0 mmol) was dissolved in dried acetonitrile (25 cm$^3$). 1-Iodoheptane (0.82 g, 3.6 mmol) was then added and the mixture heated to reflux (ca. 81° C.). After 2 hours, the reaction mixture was cooled and the bulk of the solvent removed by rotary evaporation. The phosphonium salts were then precipitated by the addition of diethyl ether and removed by filtration. The diethyl ether was removed by rotary evaporation and the yield determined by $^1H$ NMR of the reaction products. The spectroscopic yield was found to be 46%.

EXAMPLE 4

A dried sample of tetraphenylphosphonium bifluoride (2.72 g, 7.2 mmol) was dissolved in acetonitrile (25 cm$^3$). 1-Chloro-2,4-dinitrobenzene (0.76 g, 3.7 mmol) was added and the mixture brought to reflux, turning dark brown in colour. After 2 hours, the solvent was removed by rotary evaporation and the phosphonium salts preciptitated by the addition of diethyl ether, followed by removal by filtration.

The reaction yield was then determined by integration of the $^1H$ NMR spectrum of the reaction products and by comparison with the spectra of authentic samples. The yield was found to be 100%.

EXAMPLE 5

Dried tetraphenylphosphonium bifluoride (1.21 g, 3.20 mmol) was added to 3,4-dichlorobenzotrifluoride (10.01 g, 46 mmol) and the neat mixture brought to reflux, the phosphonium salt dissolving on warming the mixture. After 2 hours, the reaction mixture was allowed to cool. The crystallised phosphonium salts were then isolated by filtration.

The percentage fluorination was determined by capillary GLC using an OV101 column, the compounds being identified by comparison with authentic samples and by GCMS. Both isomers (3-fluoro and 4-fluoro) were observed, the total yield of mono fluorinated products being 16% assuming a 1 to 1 reaction stoichiometry.

EXAMPLE 6

Using the same method as in Example 5, tetraphenylphosphonium bifluoride (1.12 g, 2.9 mmol) and 3,4,5-trichlorobenzotrifluoride (8.08 g, 32.3 mmol) gave 41% monofluorinated products (all isomers being observed), assuming a 1 to 1 reaction stoichiometry. Compounds were identified by comparison of GLC retention times with those of authentic samples and by GCMS.

EXAMPLE 7

A dried sample of $Ph_4P^+HF_2^-$ (0.57 g, 1.5 mmol) was dissolved in dimethylsulphoxide (10 g) containing 2-chloro-6-nitrobenzonitrile (0.14 g, 0.75 mmol). The mixture was stirred at ambient temperature for two hours after which time analysis by gas chromatography showed 100% conversion to 2-chloro-6-fluorobenzonitrile exclusively (by comparison with a sample of authentic material). This can be compared with the same reaction carried out using rubidium fluoride rather than $Ph_4P^+HF_2^-$ which gives after 20 minutes at 150° C. a mixture of 2-chloro-6-fluorobenzonitrile and 6-nitro-2-fluorobenzonitrile. (Attina et al. Chem. Commun., 108 (1983)).

EXAMPLE 8

Tetraphenylphosphonium bifluoride (1.02 g, 2.7 mmol) that had been previously dried was dissolved in acetonitrile (15 cm$^3$) that had been dried by standing over calcium hydride for a period of several days. The solution was placed in a two neck round bottom flask, from which atmospheric water was prevented from entering by a calcium chloride drying tube. Hexafluoropropene was then gently bubbled through the solution at ambient temperature. After an induction period of one or two minutes a separate fluorocarbon layer was seen to form. During the course of the reaction, the acetonitrile solution turned from colourless to yellow to orange, and the temperature of the solution increased throughout the reaction.

After an hour, the total volume of fluorocarbon collected was 13 cm$^3$. The fluorocarbon mixture was then washed with water and dried over magnesium sulphate.

Distillation of the fluorocarbon layer show it to be composed only of dimers, a single boiling fraction being obtained with a boiling point of 45° C. Oligomerisation may also be achieved in dimethylformamide solution using tetraphenylphosphonium bifluoride under the same conditions (the DMF being previously dried over activated type 4A molecular sieves). Distillation of the products of DMF oligomerisation yielded both dimers and trimers of boiling points of ca. 45° C. and 80° C. respectively, in a ratio of 1 to 1.6 by weight. Typical product weights isolated in one hour were 3 to 5 g.

We claim:

1. A method for the preparation of organic fluorides which comprises reacting a quaternary phosphonium bifluoride with an organic compound of the formula:

Q-X$_n$ wherein Q represents an aliphatic, arylaliphatic or aromatic radical, X represents chlorine, bromine, iodine or nitro and n is an integer from 1 to 3.

2. A method according to claim 1 wherein the organic compound has the formula:

Q-X wherein Q is an alkyl, aralkyl or aryl radical.

3. A method according to claim 1 wherein the quaternary phosphonium bifluoride has the formula:

R$_3$R$^1$PHF$_2$ wherein R represents a phenyl radical and R$^1$ represents a phenyl or alkyl radical.

4. The method of claim 1 wherein the organic compound is selected from the group consisting of 1-iodoheptane, dibromomethane, 1,2-dichloroethane, benzyl chloride, benzyl bromide, 4-chlorobenzotrifluoride, 3,4-dichlorobenzotrifluoride, 3,4,5-trichlorobenzotrifluoride, 2-chloro-6-nitrobenzonitrile, 1-chloro-2,4-dinitrobenzene and 3,4-dichloronitrobenzene and the quaternary phosphonium bifluoride is selected from the group consisting of tetraphenylphosphonium bifluoride and triphenylisopropylphosphonium bifluoride.

* * * * *